United States Patent
Ortiz et al.

(10) Patent No.: US 8,357,156 B2
(45) Date of Patent: Jan. 22, 2013

(54) BALLOON TISSUE DAMAGE DEVICE

(75) Inventors: Mark S. Ortiz, Milford, OH (US);
Thomas E. Albrecht, Cincinnati, OH (US); Mark S. Zeiner, Mason, OH (US); James R. Giordano, Milford, OH (US); Matthew D. Holcomb, Lebanon, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1066 days.

(21) Appl. No.: 12/113,739

(22) Filed: May 1, 2008

(65) Prior Publication Data

US 2009/0275942 A1    Nov. 5, 2009

(51) Int. Cl.
*A61B 18/18* (2006.01)
(52) U.S. Cl. .............. 606/50; 606/41; 606/191
(58) Field of Classification Search .......... 606/33–45, 606/50, 151, 191
See application file for complete search history.

(56) References Cited

U.S. PATENT DOCUMENTS

| 6,440,128 | B1 * | 8/2002 | Edwards et al. ......... 606/41 |
| 6,558,400 | B2 | 5/2003 | Deem et al. |
| 7,892,245 | B2 | 2/2011 | Liddicoat et al. |
| 2004/0034371 | A1 | 2/2004 | Lehman |
| 2007/0118106 | A1 | 5/2007 | Utley |

FOREIGN PATENT DOCUMENTS

EP    1938758    7/2008

OTHER PUBLICATIONS

International Search Report dated Jul. 30, 2009; International Application No. PCT/US2009/042279.

* cited by examiner

*Primary Examiner* — Linda Dvorak
*Assistant Examiner* — Amanda Scott
(74) *Attorney, Agent, or Firm* — Welsh Flaxman & Gitler LLC

(57) ABSTRACT

An inflatable medical instrument for tissue damage in gastric reduction surgery includes a main chamber composed of a biocompatible material capable of being selectively inflated. The medical instrument also includes a longitudinally extending tab member secured to an outer surface of the main chamber, a series of suction holes are formed along the tab member and an electrode is mounted on the tab member. The present invention also provides a method for forming a tissue junction used in defining a gastric pouch including damaging opposed tissue layers, apposing the tissue layers and fastening the tissue layers to allow the tissue layers to heal together.

7 Claims, 11 Drawing Sheets

BALLOON TISSUE DAMAGE DEVICE

BACKGROUND OF THE INVENTION

1. Field of the Invention

The present invention relates generally to gastric reduction surgery and, more particularly, to a method for reducing gastric cavity volume by forming one or more mucosa-to-mucosa contact folds. In particular, the invention relates to a method and apparatus for damaging gastric tissue to enhance the performance of gastric reduction surgery.

2. Description of the Related Art

Obesity is a medical condition affecting more than 30% of the population in the United States. Obesity affects an individual's personal quality of life and contributes significantly to morbidity and mortality. Obese patients, i.e., individuals having a body mass index ("BMI") greater than 30, often have a high risk of associated health problems (e.g., diabetes, hypertension and respiratory insufficiency), including early death. With this in mind, and as those skilled in the art will certainly appreciate, the monetary and physical costs associated with obesity are substantial. In fact, it is estimated the costs relating to obesity are in excess of 100 billion dollars in the United States alone. Studies have shown that conservative treatment with diet and exercise alone may be ineffective for reducing excess body weight in many patients.

Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure a small stomach pouch is separated from the remainder of the gastric cavity and attached to a resected portion of the small intestine. This resected portion of the small intestine is connected between the "smaller" gastric cavity and a distal section of small intestine allowing the passage of food therebetween. The conventional RYGB procedure requires a great deal of operative time. Because of the degree of invasiveness, post-operative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing a feeling of satiety. A band is placed around the stomach near the junction of the stomach and esophagus. The small upper stomach pouch is filled quickly, and slowly empties through the narrow outlet to produce the feeling of satiety. Other forms of bariatric surgery that have been developed to treat obesity include Fobi pouch, bilio-pancreatic diversion and gastroplasty or "stomach stapling". It is also known to create mucosa-to-mucosa folds along the interior surface of the gastric cavity in the performance of gastric reduction surgery.

With the foregoing in mind, it is desirable to provide surgical weight loss procedures (and associated medical instruments) that present few potential complications, are minimally invasive to the patient, and allow for a quick recovery and less scarring. The present invention improves upon prior procedures by providing a method and medical instrument allowing for improved formation of a plication within the gastric cavity.

SUMMARY OF THE INVENTION

It is, therefore, an object of the present invention to provide an inflatable medical instrument for tissue damage in gastric reduction surgery. The medical instrument includes a main chamber composed of a biocompatible material capable of being selectively inflated. The medical instrument also includes a longitudinally extending tab member secured to an outer surface of the main chamber, a series of suction holes are formed along the tab member and an electrode is mounted the tab member.

It is also an object of the present invention to provide an inflatable medical instrument wherein the main chamber is secured to an inflation port for selective inflation thereof.

It is a further object of the present invention to provide an inflatable medical instrument wherein the tab member extends radially outwardly from the outer surface of the main chamber for contact with an internal surface of a gastric cavity.

It is another object of the present invention to provide an inflatable medical instrument wherein the suction holes are formed along both a first side of the tab member and a second side of the tab member.

It is also an object of the present invention to provide an inflatable medical instrument wherein the first side of the tab member and the second side of the tab member are substantially opposed to permit drawing opposed gastric cavity tissue into contact therewith for damaging tissue.

It is a further object of the present invention to provide an inflatable medical instrument wherein the tab member is coupled to a suction lumen.

It is another object of the present invention to provide an inflatable medical instrument wherein the electrode is positioned on both a first side of the tab member and a second side of the tab member.

It is also an object of the present invention to provide an inflatable medical instrument wherein the electrode is energized by a bipolar or a monopolar source.

It is a further object of the present invention to provide an inflatable medical instrument wherein current for the electrode is transmitted through wires of a sufficient length to extend from the tab member when it is inserted within the gastric cavity to a location external of the patient undergoing treatment.

It is also an object of the present invention to provide an inflatable medical instrument wherein the main chamber is composed of a biocompatible resilient material.

It is another object of the present invention to provide a method for forming a tissue junction used in defining a gastric pouch including damaging opposed tissue layers, apposing the tissue layers and fastening the tissue layers to allow the tissue layers to heal together.

It is also an object of the present invention to provide a method wherein the tissue layers are the anterior cavity wall and the posterior cavity wall.

It is another object of the present invention to provide a method wherein the step of damaging includes contacting the tissue layers with electrodes.

It is a further object of the present invention to provide a method wherein the step of fastening includes applying adhesive to the tissue layers.

It is also an object of the present invention to provide a method wherein the step of apposing includes applying suction to draw the tissue layers together.

It is another object of the present invention to provide a method wherein the step of damaging the tissue layers includes applying suction to draw the tissue layers together.

It is a further object of the present invention to provide a method wherein the step of damaging also includes contacting the tissue layers with electrodes.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Figure 1:
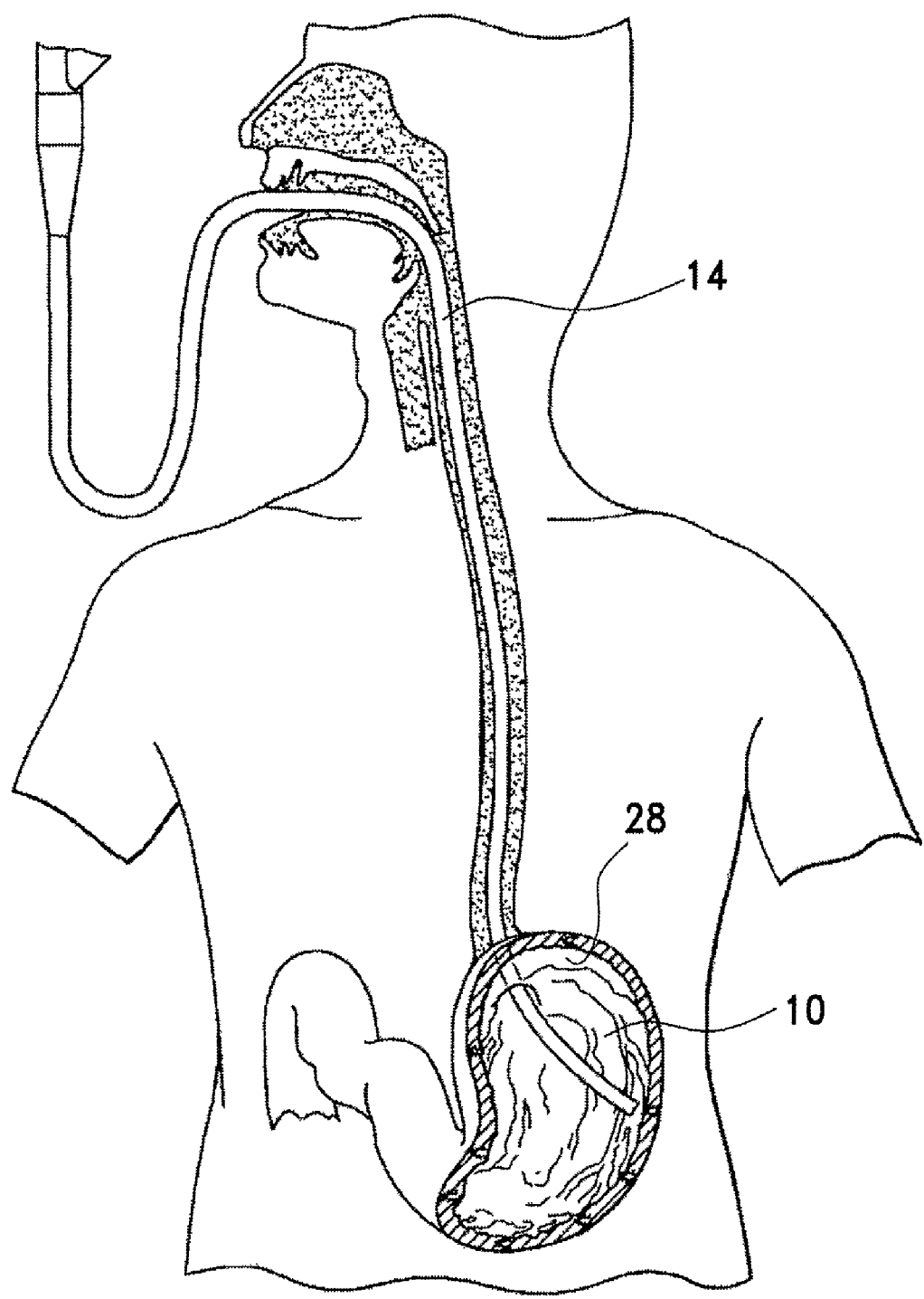
FIGS. 1 and 2 show steps associated with accessing the gastric cavity for reducing the gastric cavity in accordance with the present invention.
Figure 2:
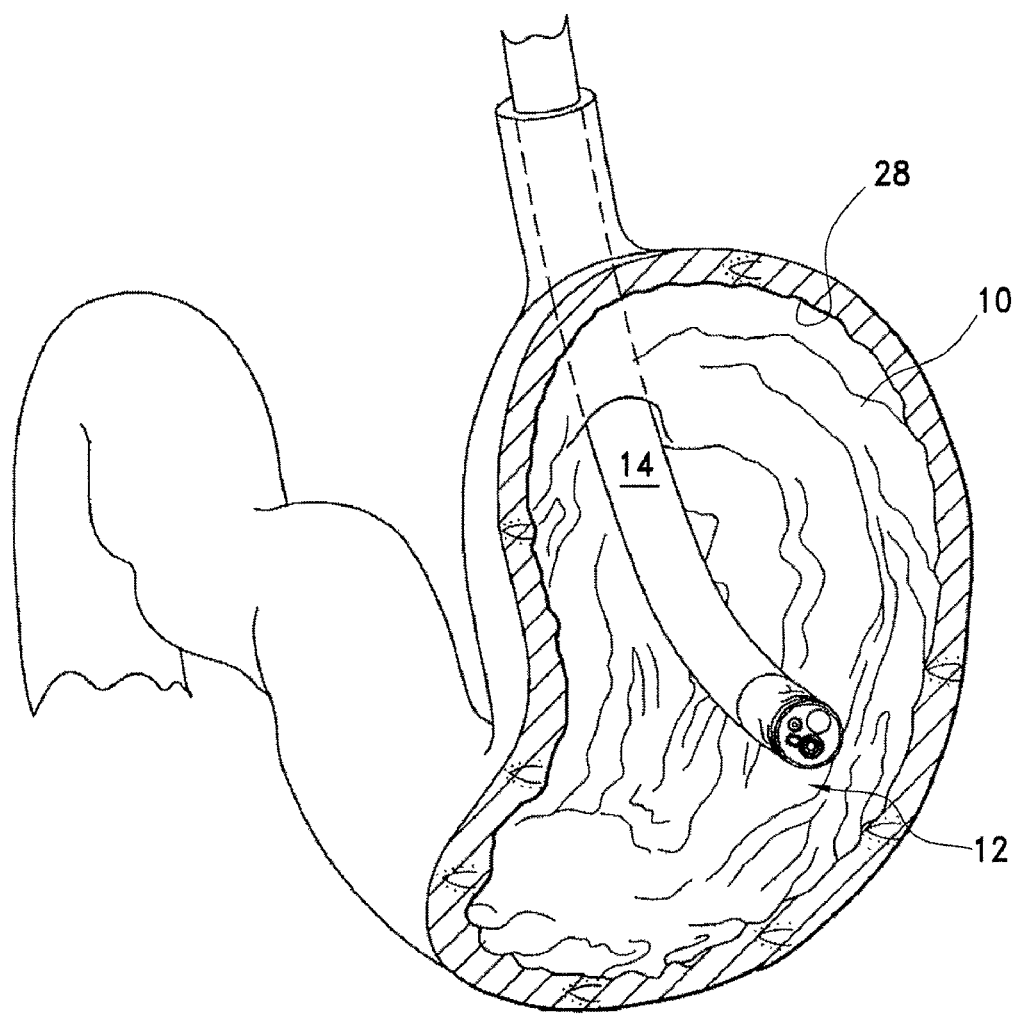
Figure 3:
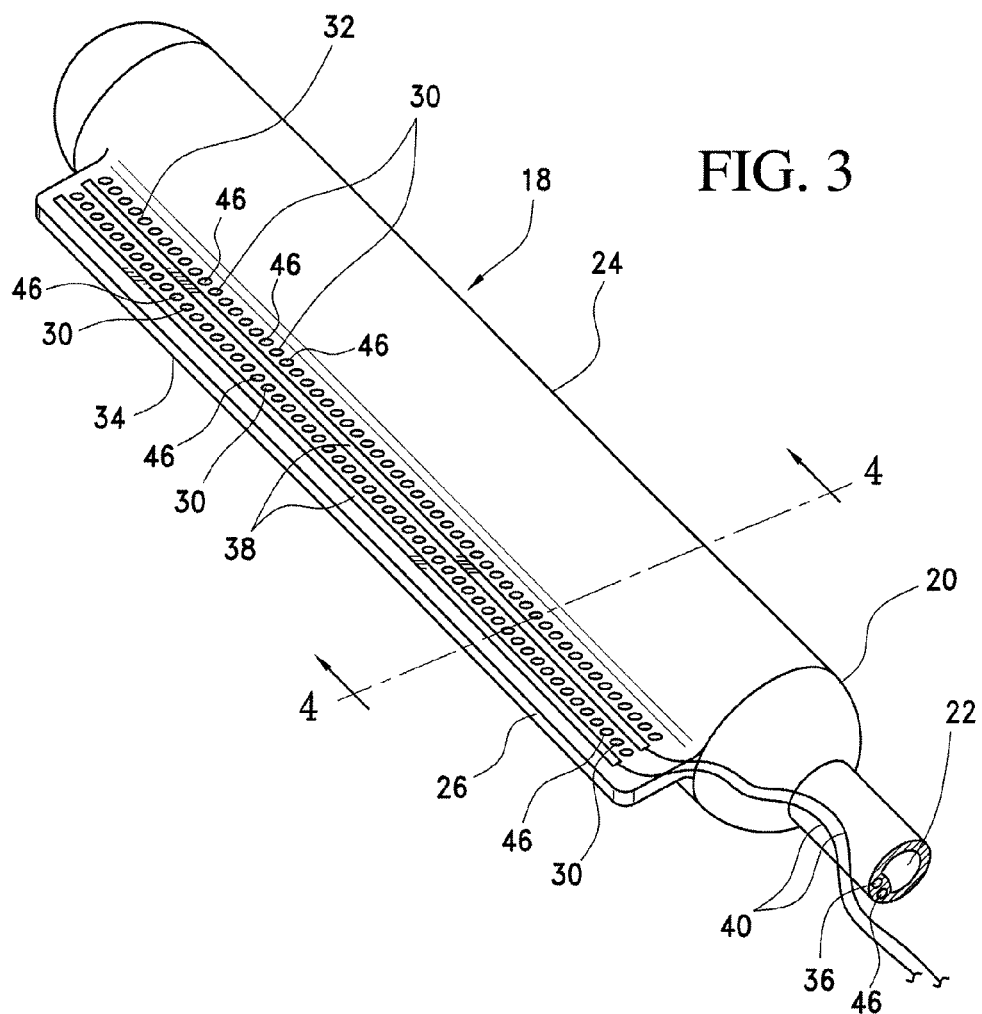
FIG. 3 is a perspective view of the present medical instrument.
Figure 4:
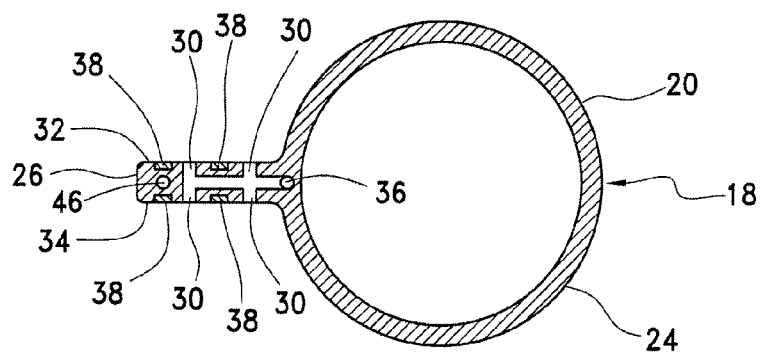
FIG. 4 is a cross sectional view along the line 4-4 in FIG. 3.

Referring now to the drawing figures, in which like numerals indicate like elements throughout the views, FIG. 1 is a diagrammatic view of a patient during an endoscopic procedure for creating junctions, in particular, mucosa-to-mucosa junctions in gastric wall 28. The remaining figures relate to coupling the anterior cavity wall 12 and the posterior cavity wall 13 of the gastric cavity 10 during gastric reduction surgery for the creation of a gastric pouch 50 which reduces effective stomach volume. As used throughout the present disclosure, the term endoscopic is intended to refer to medical procedures in which the body is accessed through a natural orifice of the body (for example, transorally) and the term laparoscopic is intended to refer to medical procedures in which the body is accessed through a surgically created opening (for example, through a trocar inserted through the abdomen wall 15). While the present disclosure focuses upon the formation of a junction between the anterior cavity wall and the posterior cavity wall, the present invention could be utilized in joining tissue in various manners as desired by the medical practitioner.

In accordance with a preferred embodiment of the present invention, a mucosa-to-mucosa junction is between the anterior cavity wall 12 and the posterior cavity wall 13 through an endoscopic approach. By creating the fold which defines a gastric pouch 50 between the anterior cavity wall 12 and the posterior cavity wall 13 of the gastric cavity 10 a pouch 50 is produced resulting in a reduction in the volume of the gastric cavity 10 which results in satiety with the intake of smaller food volumes and ultimately a loss of weight.

In accordance with the method employed in accordance with a preferred embodiment of the present invention, visualization of the one or more mucosa-to-mucosa junction locations is achieved by passing an endoscope 14 into the interior of the gastric cavity 10. As shown in FIG. 1, a flexible endoscope 14 is passed transesophageally into the gastric cavity 10. The endoscope 14 provides insufflation, illumination, and visualization of the gastric cavity 10, as well as a passageway into the gastric cavity 10. Using the endoscope 14 to visualize the desired location for formation of a pouch may reduce or eliminate the need for visualization on the outside of the gastric cavity 10.

In accordance with a preferred embodiment of the present invention and with reference to FIGS. 3 to 11, the mucosa-to-mucosa junction used in defining a gastric pouch is best achieved by damaging the mucosal layer (or other gastric tissue layer to be apposed) and then apposing and fastening the injured (that is, treated) tissue together to allow it to heal together. In accordance with a preferred embodiment of the present invention, and with reference to FIG. 3, an inflatable medical instrument 18 is used in damaging the mucosal tissue prior to apposition of the tissue as detailed herein. The inflatable medical instrument 18 includes a main chamber 20 composed of a biocompatible resilient material capable of being selectively inflated like a balloon for utilizing in the manner described herein. The main chamber 20 is secured to an inflation port 22 which is of a sufficient length to extend from the main chamber 20 when it is inserted within the gastric cavity 10 to a location external of the patient undergoing the present procedure. Once the main chamber 20 is positioned at a desired location within the gastric cavity 10, the inflation port 22 allows for the establishment of a predictable pouch size within the gastric cavity 10 by expanding the main chamber 20 to a predetermined size and shape defining a template of the pouch size desired in accordance with the specific needs of a patient.

Secured to the outer surface 24 of the main chamber 20 is a longitudinally extending tab member 26. The tab member 26 extends radially outwardly from the outer surface 24 of the main chamber 20 for contact with the internal surface 28 of the gastric cavity 10. A series of suction holes 30 and adhesive ports 46 are formed along the tab member 26. As shown, the suction holes 30 and adhesive ports 46 alternate in order to provide a compact design. The suction holes 30 and adhesive ports 46 are formed along both a first side 32 of the tab member 26 and a second side 34 of the tab member 26, wherein the first and second sides 32, 34 of the tab member 26 are substantially opposed to permit drawing opposed gastric cavity tissue into contact therewith for damaging tissue in accordance with the present invention. The tab member 26 is coupled to a suction lumen 36 which extends along the inflation port 22, and is, therefore, of a sufficient length to extend from the tab member 26 when it is inserted within the gastric cavity 10 to a location external of the patient undergoing the present procedure.

In addition to the suction holes 30 formed along the tab member 26, first and second elongated electrodes 38 are respectively mounted on both the first side 32 and the second side 34 of the tab member 26. In accordance with a preferred embodiment, energy mechanisms for the electrodes 38 include bipolar or monopolar sources. The current for the first and second electrodes 38 is transmitted through wires 40 extending along the suction lumen 36 to the tab member 26. The wires 40 are, therefore, of a sufficient length to extend from the tab member 26 when it is inserted within the gastric cavity 10 to a location external of the patient undergoing the present procedure. Because of the parallel arrangement of the first and second electrodes 38, and as will be discussed below in greater detail, the tissue between the first and second electrodes 38 is damaged upon the application of current to the first and second electrodes 38.

Figure 5:
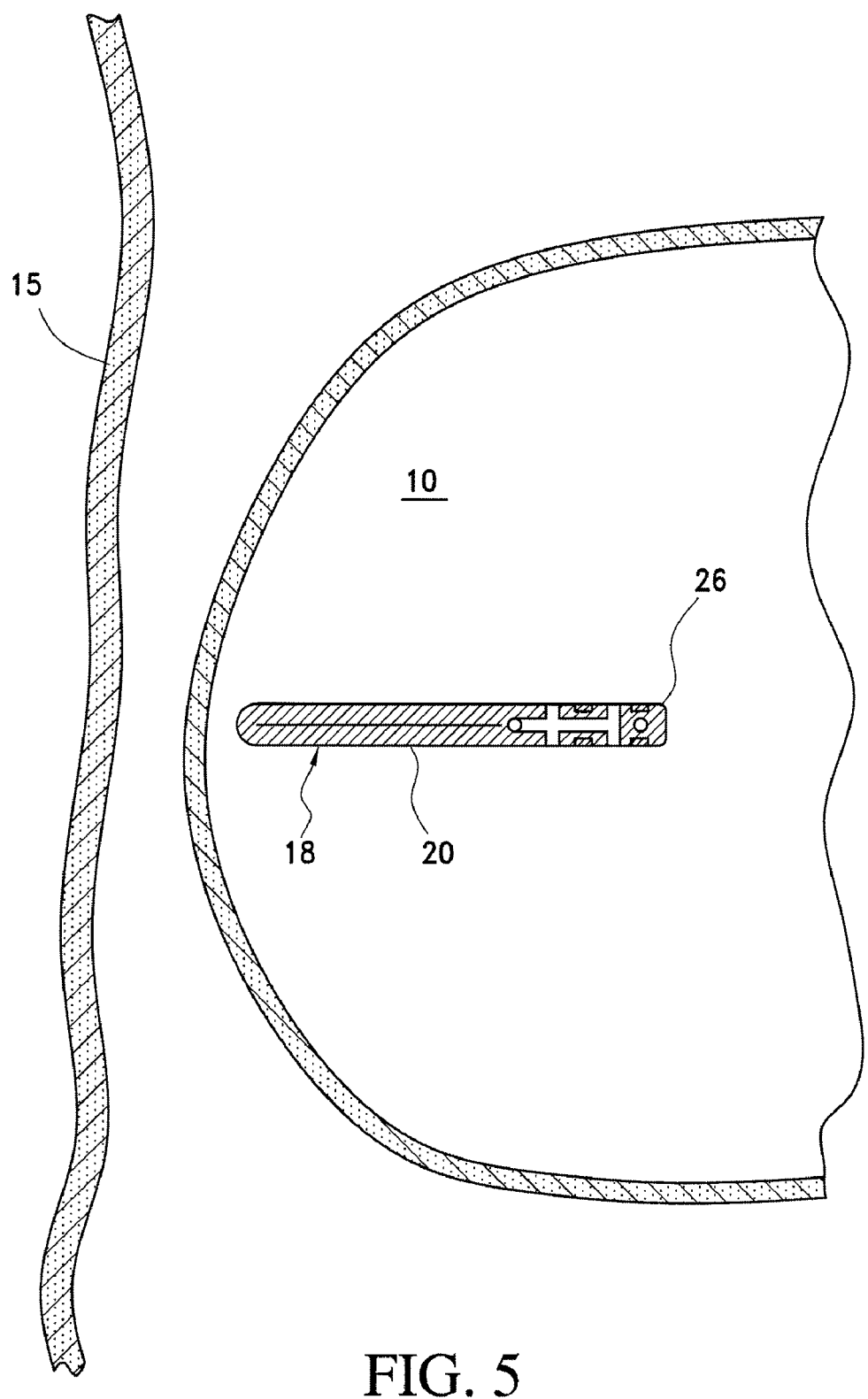
FIGS. 5 to 11 shows the steps associated with the use of the present medical instrument in forming a mucosa-to-mucosa fold along the stomach wall.
Figure 6:
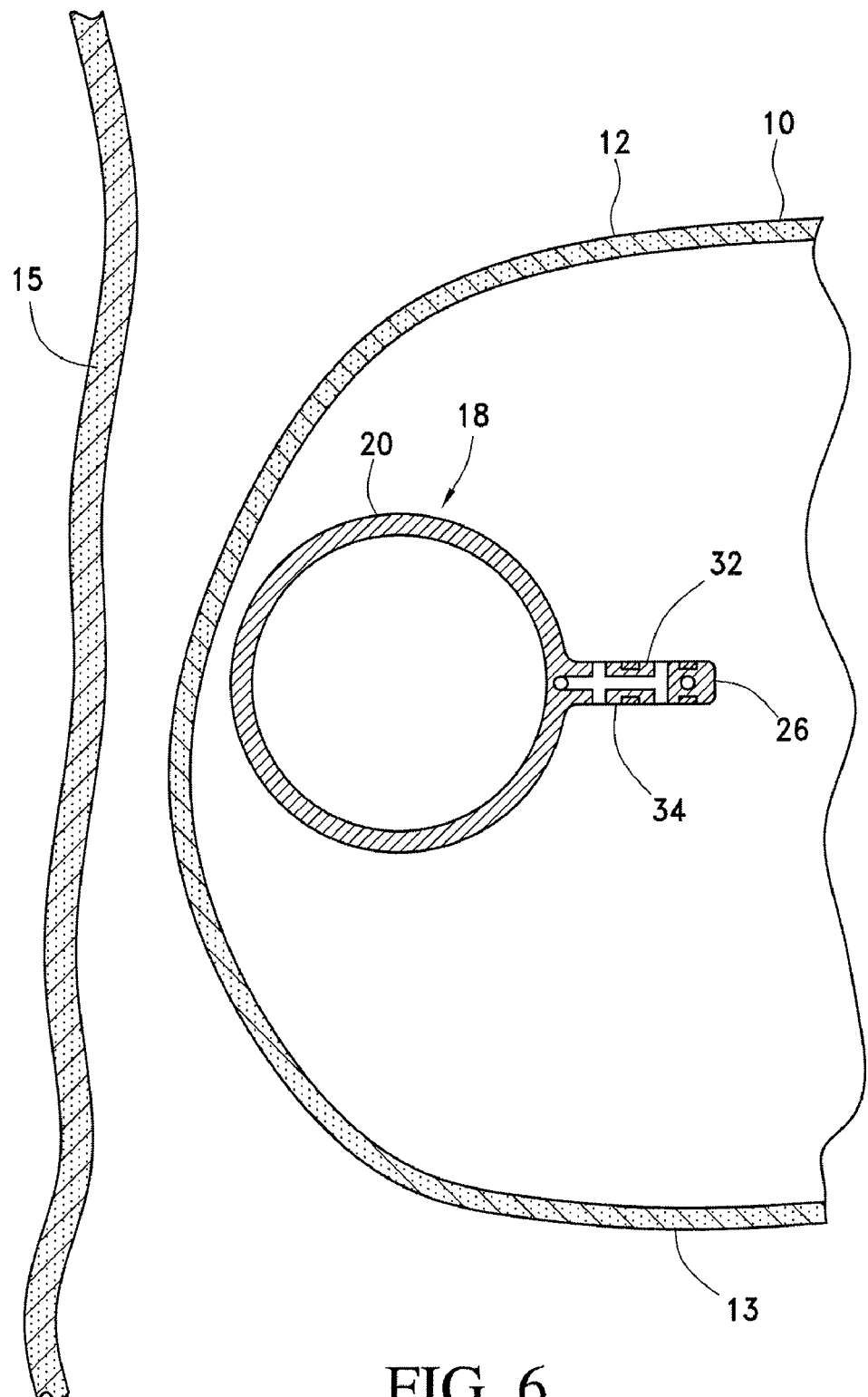
Figure 7:
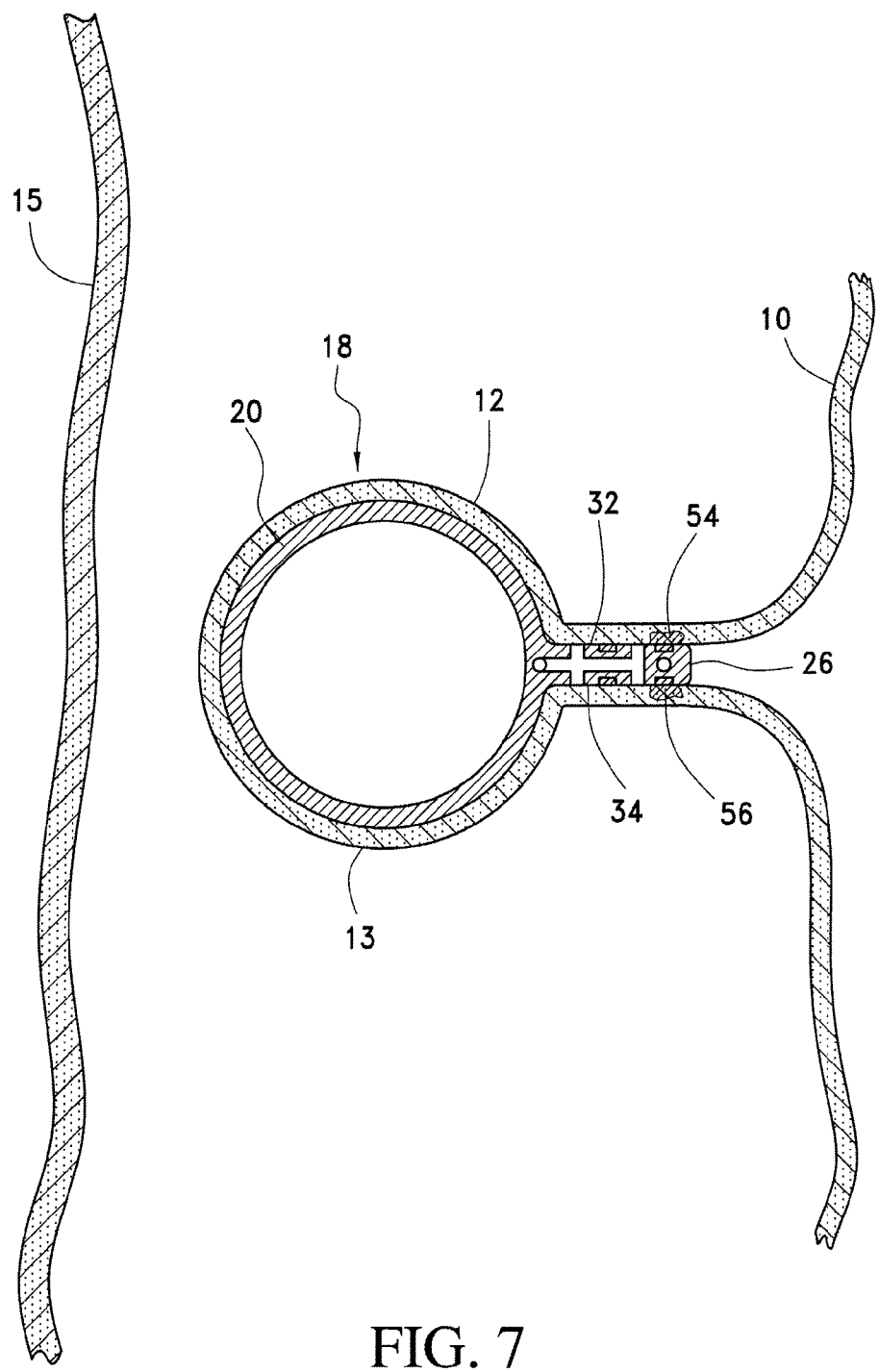
Figure 8:
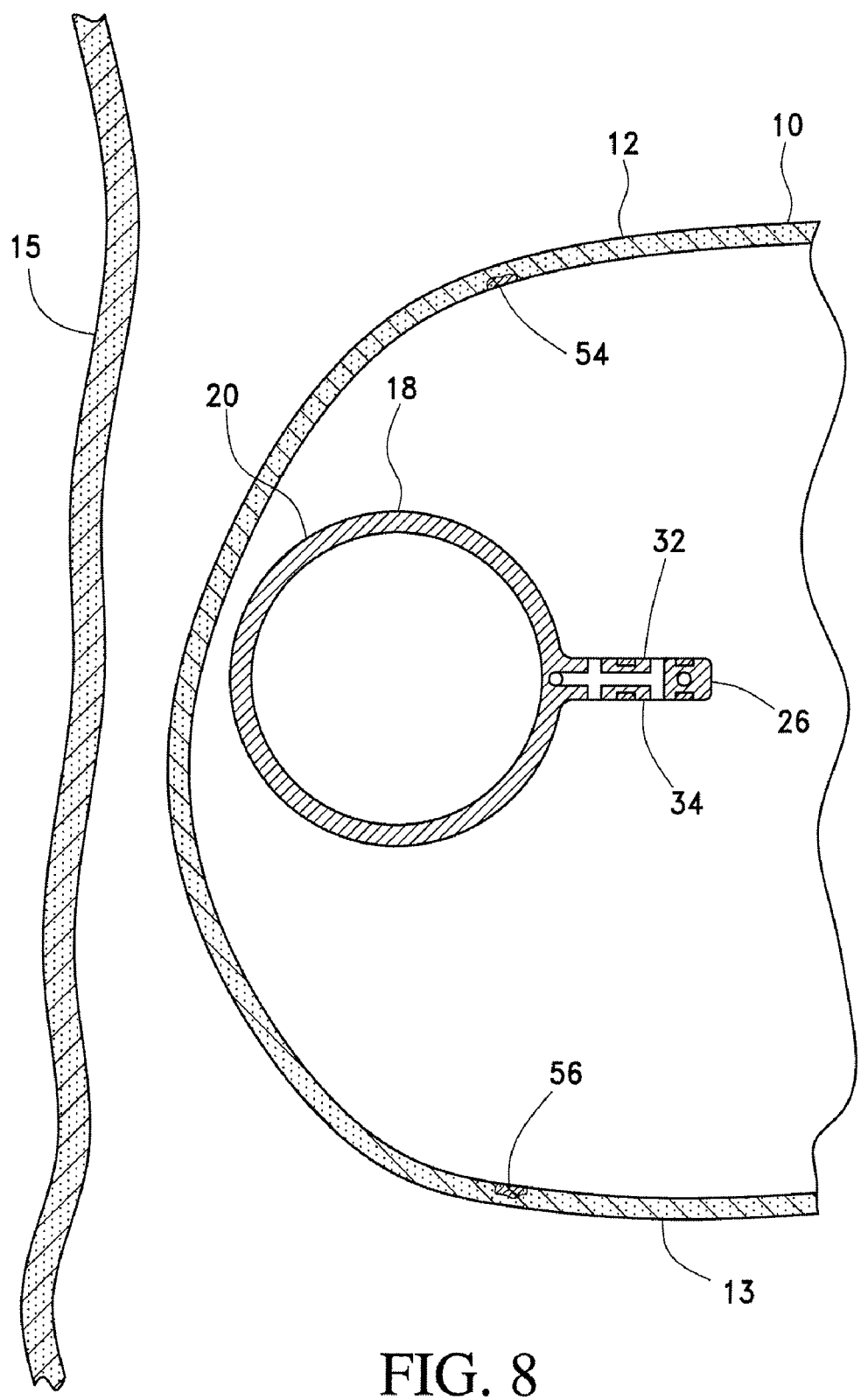
Figure 9:
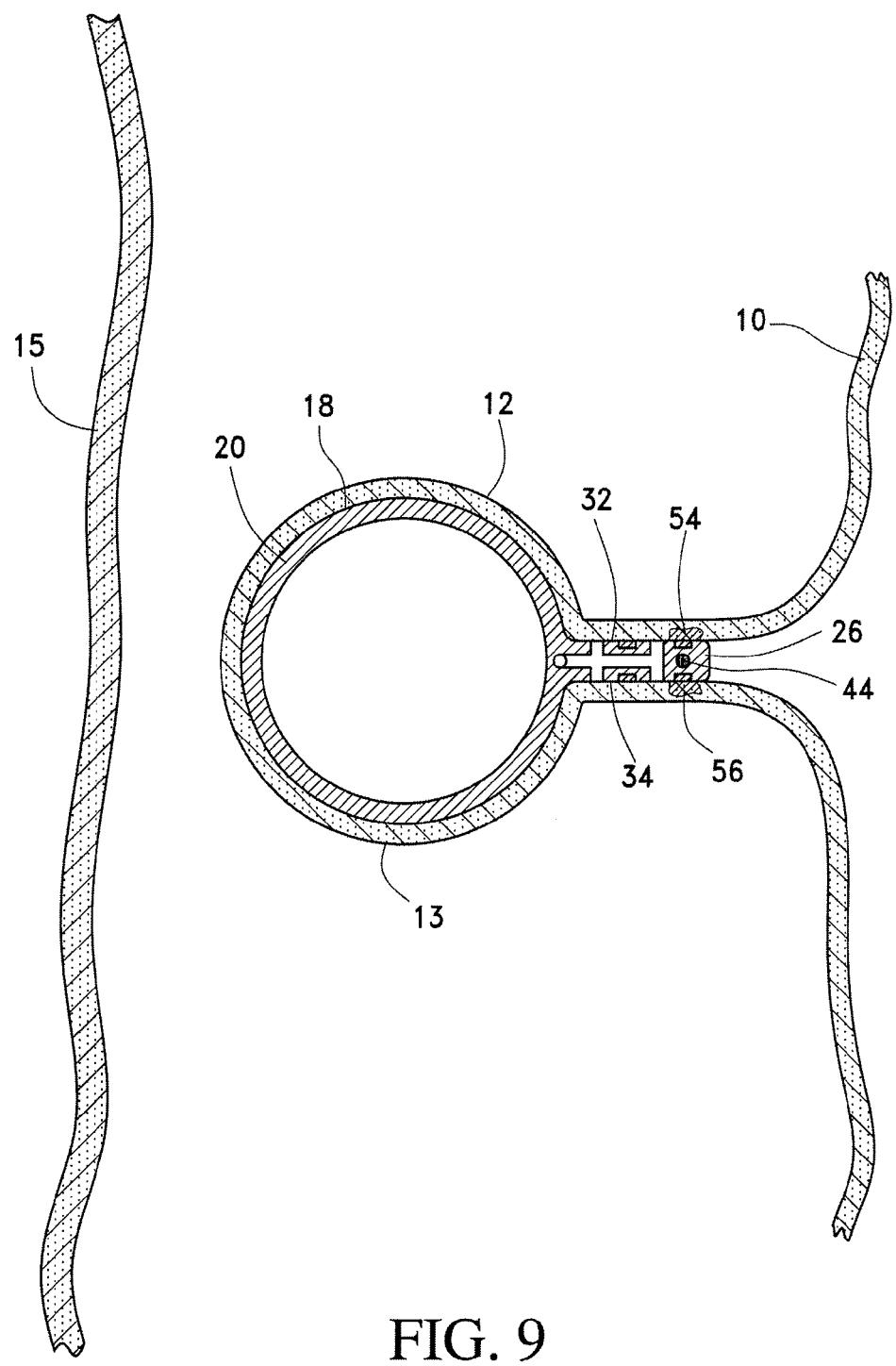
Figure 10:
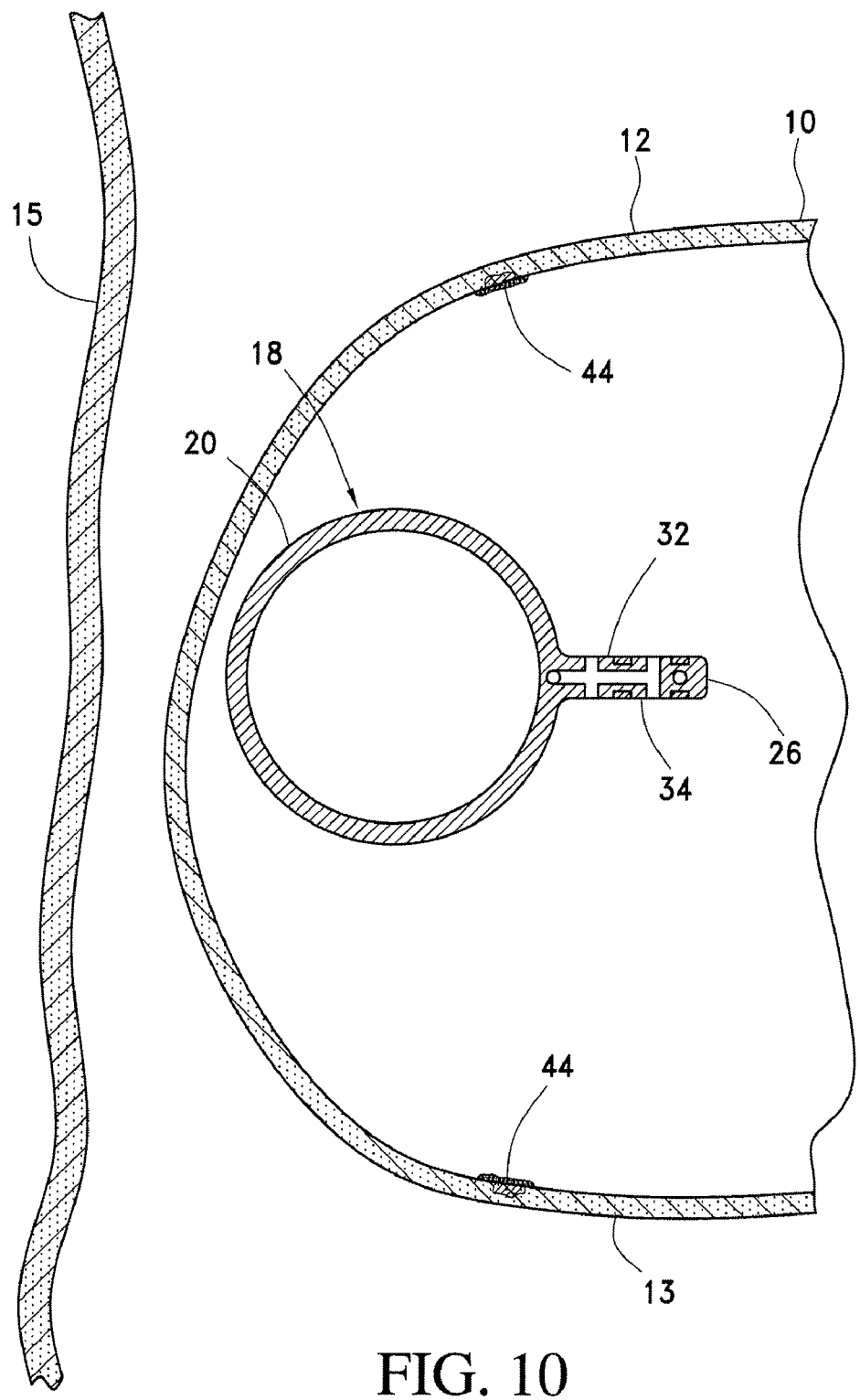
Figure 11:
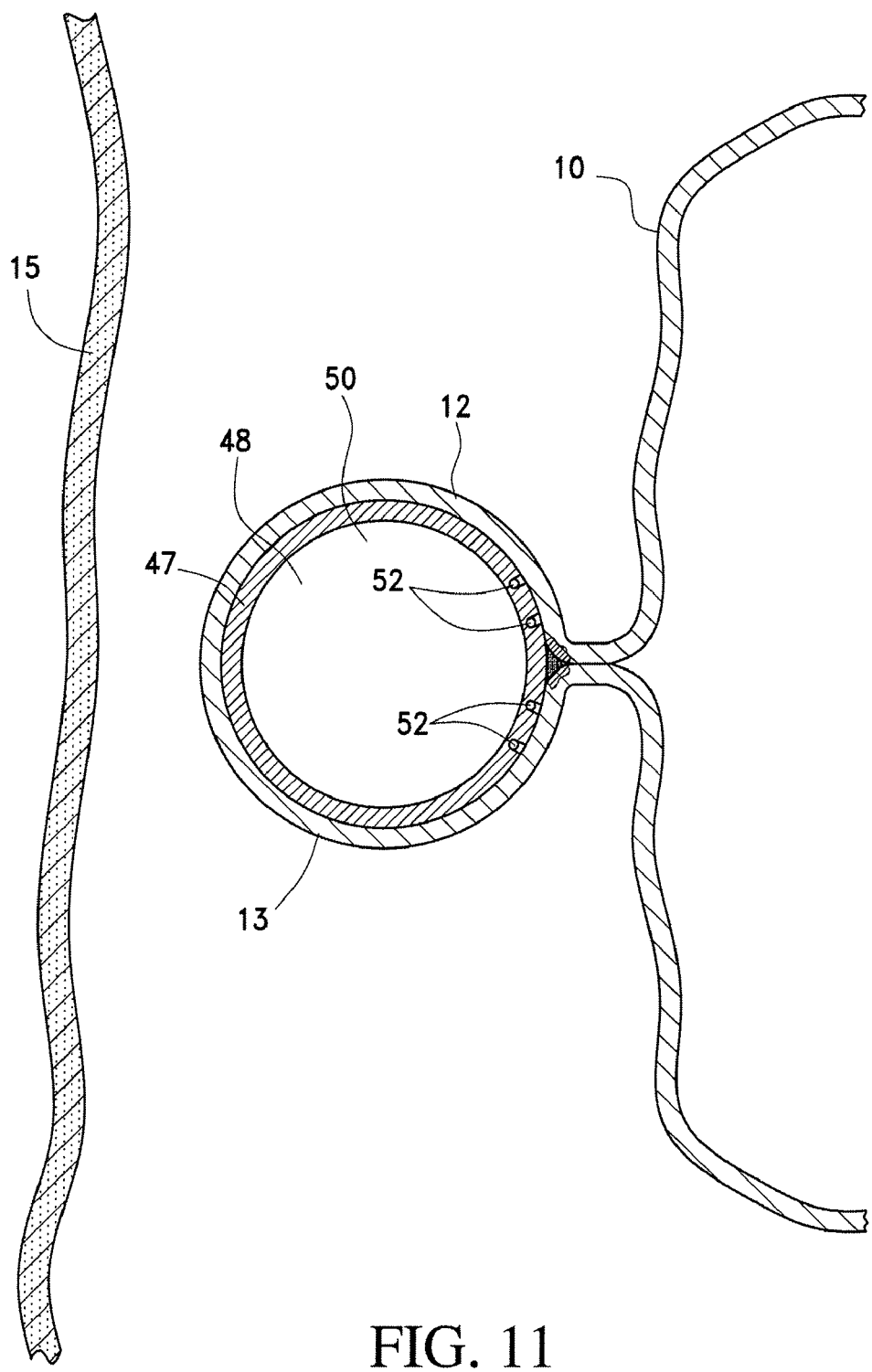

In practice, and with reference to FIGS. 5 to 11 in relationship to the abdomen wall 15, the main chamber 20 of the medical instrument 18 is inserted transesophageally into the gastric cavity 10 in a deflated condition (see FIG. 5). Once the main chamber 20 is properly positioned within the gastric cavity 10 preferably along the lesser curve, the main chamber 20 is inflated using a pressure source (not shown) coupled to the inflation port 22 to establish a predetermined main chamber 20 size and shape desired for the creation of a gastric pouch in accordance with the present invention (see FIG. 6). Suction is then applied to the suction holes 30 drawing the anterior cavity wall 12 and the posterior cavity wall 13 toward the suction holes 30, which are isolated from the main chamber 20 formed along the first side 32 and the second side 34 of the tab member 26. The suction on the suction holes 30 is provided by a vacuum source (not shown) connected to the suction lumen 36. Once the tissue of the anterior cavity wall 12 and the posterior cavity wall 13 is suctioned down into engagement with the tab member 26, the electrodes 38 are energized applying energy to the tissue and creating damaged lines 54, 56 of tissue (see FIG. 7). The suction is released and the gastric cavity tissue moves away from the tab member 26 (see FIG. 8).

Figure 12:
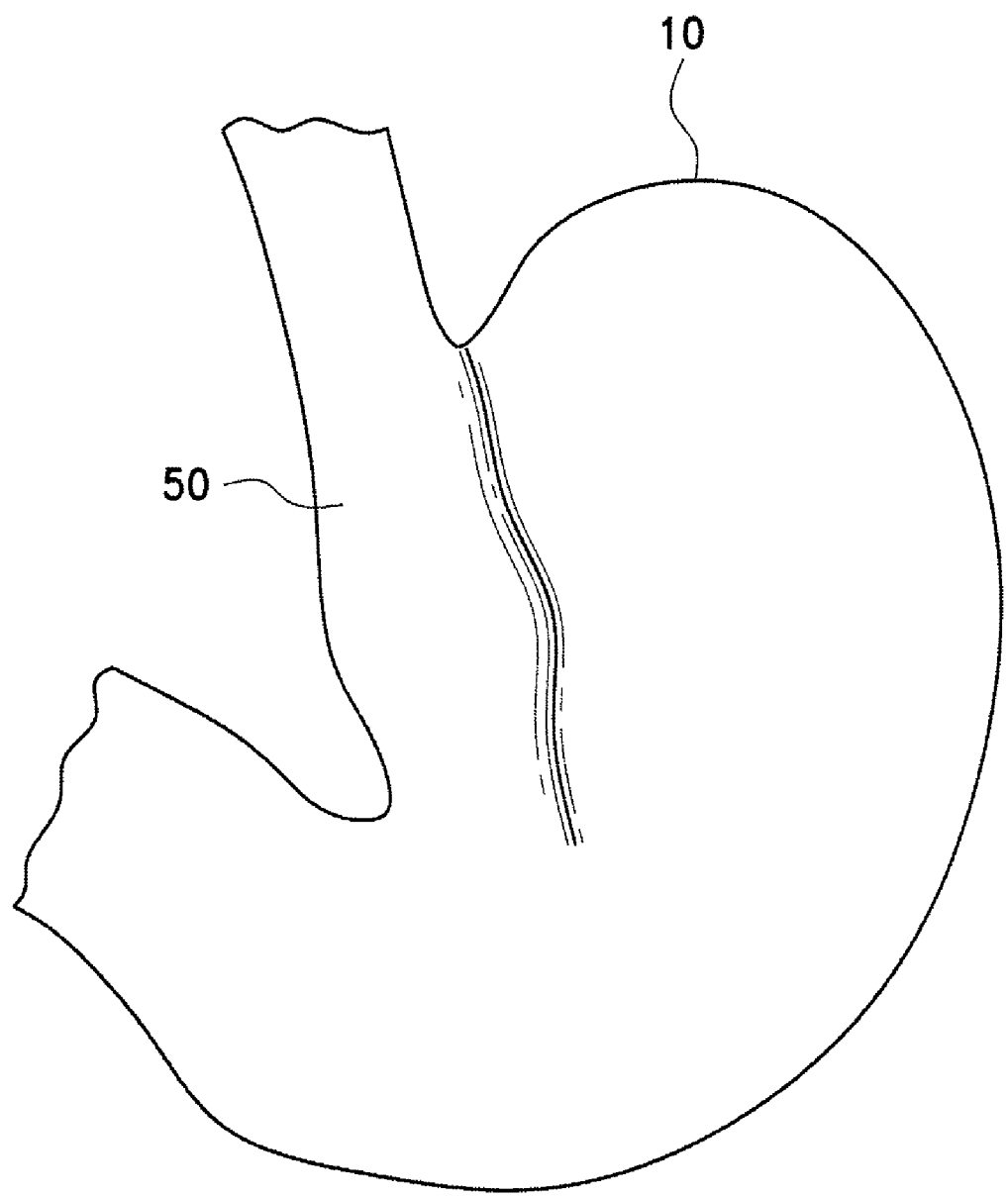
FIG. 12 is a schematic showing formation of a pouch in accordance with the present invention.

Thereafter, suction is again applied to the suction ports, drawing the damaged tissue together once again. An adhesive 44 such as cyanoacrylate or active PEG adhesive is then dispensed via the alternating adhesive application ports 46 along the first and second sides 32, 34 of the tab member 26. Thereafter, the suction applied to the suction ports 30 is removed allowing for release of the tissue from the inflatable medical instrument 18. The inflatable medical instrument 18 may then be deflated and removed. Thereafter a suction device 47 of a size similar to the main chamber 20 is inserted and then inflated and positioned at approximately the same location as the main chamber 20 of the inflatable medical instrument 18 previously discussed. The suction device 47 also includes an inflatable main chamber 48 that is shaped substantially similar to the main chamber 20 of the inflatable medical instrument 18 and as such occupies a space similar to that of the inflatable medical instrument 18. The suction device 47 also includes suction ports 52 such that when suction is applied thereto the anterior cavity wall 12 and posterior cavity wall 13 are drawn together bringing the damaged line of mucosal tissue to which adhesive has previously been applied together (see FIG. 11). Continued application of suction (for approximately 60 seconds) allows the adhesive to set creating a gastric pouch 50 reducing stomach volume (see FIG. 12).

It is further contemplated that the suction applied via suction holes 30 can be controlled such that adhesive can be applied via ports 46 as tissue is loosely held against tab member 26, thereby eliminating a release step in the method.

Another method for reinforcing the mucosa-to-mucosa junction is to inject a chemical solution into the cavity wall. The injected solution toughens the surrounding tissue area to decrease the likelihood of the T-tag anchors eroding through the cavity wall. Chemical solutions (or bulking agents) suitable for this application include chiersoants, tgf-bea, keratin, PMMA (polymethym-ethacry-late), among others. Medications that promote healing, such as Vitamin C which raises ascorbic acid levels in the body may also be used to aid in the rapid and durable mucosa-to-mucosa healing. Such medications may also be delivered through the buttress, anchors, or taken orally.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that the device is sterilized. This can be done by any number of ways known to those skilled in the art including beta or gamma radiation, ethylene oxide, and/or steam.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An inflatable medical instrument for tissue damage in gastric reduction surgery, comprising:
   a main chamber composed of a biocompatible material capable of being selectively inflated;
   a longitudinally extending tab member secured to an outer surface of the main chamber, the tab member extends radially outwardly from the outer surface of the main chamber for contact with an internal surface of a gastric cavity and includes opposed first and second sides;
   a series of suction holes are formed along both the first and second sides of the tab member and electrodes are mounted on both the first and second sides of the tab member.

2. The inflatable medical instrument according to claim 1, wherein the main chamber is secured to an inflation port for selective inflation thereof.

3. The inflatable medical instrument according to claim 1, wherein the first side of the tab member and the second side of the tab member are substantially opposed to permit drawing opposed gastric cavity tissue into contact therewith for damaging tissue.

4. The inflatable medical instrument according to claim 3, wherein the tab member is coupled to a suction lumen.

5. The inflatable medical instrument according to claim 1, wherein the electrode is energized by a bipolar or a monopolar source.

6. The inflatable medical instrument according to claim 1, wherein current for the electrode is transmitted through wires of a sufficient length to extend from the tab member when it is inserted within a gastric cavity to a location external of the patient undergoing treatment.

7. The inflatable medical instrument according to claim 1, wherein the main chamber is composed of a biocompatible resilient material.

* * * * *